United States Patent [19]

Frank

[11] 4,185,502
[45] Jan. 29, 1980

[54] TRANSDUCER COUPLING APPARATUS

[76] Inventor: Ralph Frank, 910 East Ave., Onalaska, Wis. 54601

[21] Appl. No.: 840,583

[22] Filed: Oct. 11, 1977

[51] Int. Cl.² ............... G01N 29/00; A01B 5/00
[52] U.S. Cl. ....................... 73/644; 73/624; 128/660
[58] Field of Search .......... 73/620, 622, 624, 633, 73/644; 128/2 V, 2.05 Z

[56] References Cited

U.S. PATENT DOCUMENTS

| | | | |
|---|---|---|---|
| 2,789,557 | 4/1957 | Davis | 128/24 A |
| 2,852,019 | 9/1958 | Fry | 128/24 A |
| 2,920,617 | 1/1960 | Boiarsky | 128/24 A |
| 2,992,553 | 7/1961 | Joy | 73/644 X |
| 3,237,623 | 3/1966 | Gordon | 128/24 A |
| 3,401,690 | 9/1968 | Martin | |
| 3,480,002 | 11/1969 | Flaherty et al. | 128/2 V |
| 3,631,714 | 1/1972 | Crassman et al. | 73/644 |
| 3,867,929 | 2/1975 | Joyner et al. | 128/24 A X |
| 3,927,661 | 12/1975 | Takemura | 73/621 X |
| 4,059,098 | 11/1977 | Murdock | 73/644 X |

OTHER PUBLICATIONS

"Clinical Application of High Speed B Mode Echocardiography," by Kambe et al. from Journal of Clinical Ultrasound, vol. 5, No. 3, pp. 202–207.

Primary Examiner—Donald Watkins
Attorney, Agent, or Firm—Merchant, Gould, Smith, Edell, Welter & Schmidt

[57] ABSTRACT

Apparatus for coupling an ultrasonic energy transducer to a target object, such as a human patient, through an energy transmitting liquid. The coupling apparatus comprises an open top container for holding the energy transmitting liquid. The transducer extends through the open container top for immersion below the surface of the liquid and for selective movement relative to the container. A support member is provided for holding the container in contact with the patient. The support member has a ring for rotatably receiving and supporting the container. The ultrasonic wave output from the transducer may be directed to different portions of the patient by selective rotation of the container and/or by repositioning the transducer within the container.

7 Claims, 3 Drawing Figures

U.S. Patent　　Jan. 29, 1980　　4,185,502
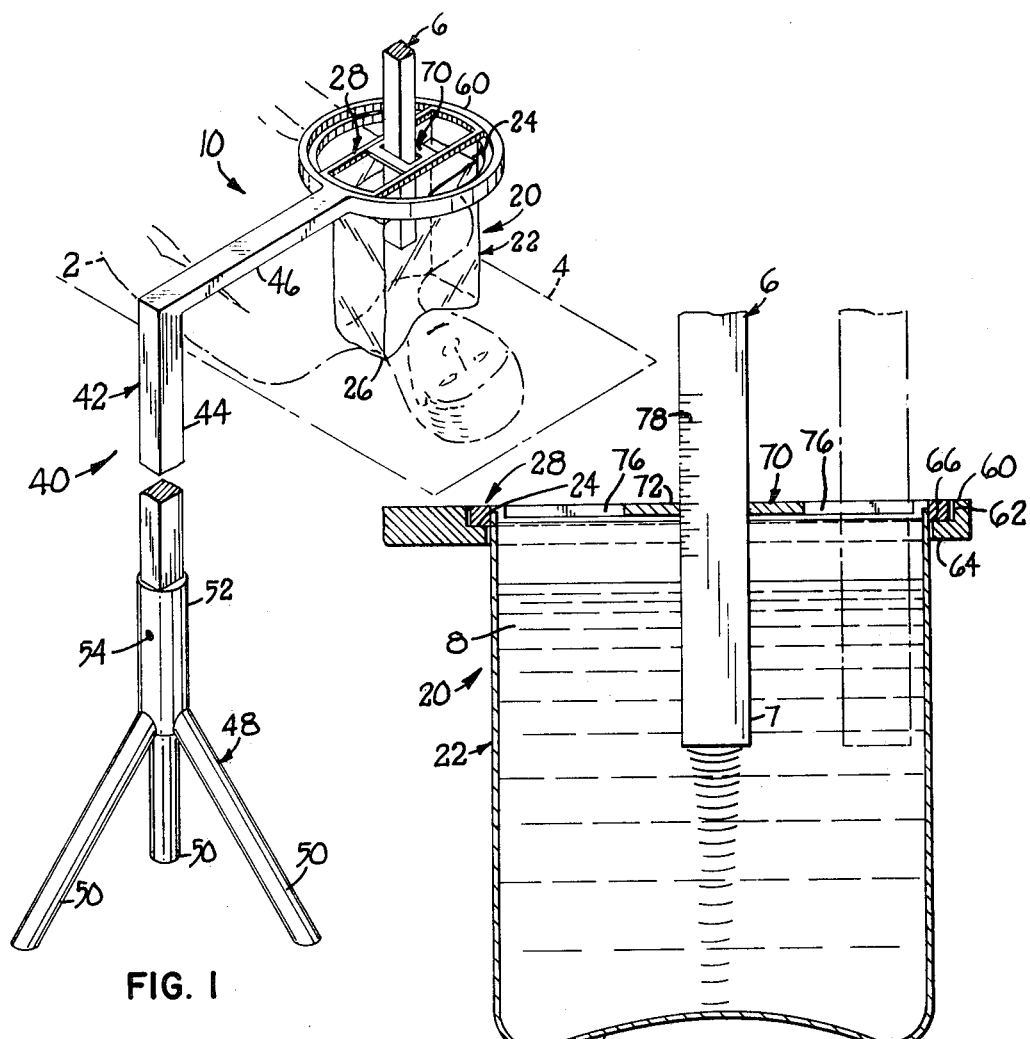
FIG. 1
FIG. 3
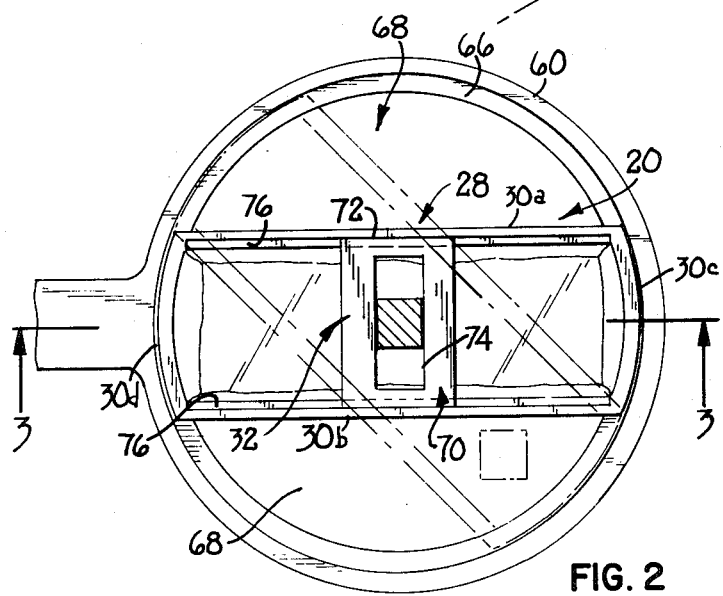
FIG. 2

TRANSDUCER COUPLING APPARATUS

BACKGROUND OF THE INVENTION

1. Field of the Invention

The present invention relates to an apparatus which utilizes an energy transmitting liquid for coupling an ultrasonic energy transducer to a target object. One aspect of the present invention is an apparatus for adjustably supporting a container holding the energy transmitting liquid to ensure easy adjustment of the container relative to the target object (i.e. relative to a human body).

2. Description of the Prior Art

Ultrasonic sound waves are those mechanical displacement pressure waves having a frequency above the human ear's audibility limit of approximately 20,000 cycles per second. Such ultrasonic waves have extremely good transmission characteristics through water and other liquids, as well as through many solid objects. In other words, ultrasonic waves can travel over lond distances through such transmitting media without large power losses. However, air and most other gases are not suitable for transmitting ultrasonic waves over long distances because of the rapid power losses which are encountered.

One common use of ultrasonic waves is in sonar applications. Sonar enables one to locate objects submerged in water, such as submarines, by transmitting ultrasonic waves toward the suspected location of the submerged object and then detecting the reflections of the waves from the object. Another use of ultrasonic radiation is to locate flaws in various structural members such as metal I-beams and the like.

Ultrasonic energy has also been widely used in the medical field. One such application involves the use of ultrasonic transducers in diagnostic instruments. In such an application, ultrasonic transducers are used to scan various organs of the human body such as the heart. When the reflections of the ultrasonic waves from the target body organ are recorded and correlated, they give an accurate cross section or profile of the particular organ being studied. This cross section enables a physician to locate abnormalities in the organ. In one sense, such an ultrasonic application is essentially a sonar-type use of ultrasonic waves as applied to the human body.

Another medically related use for ultrasonic energy is in the treatment of various diseased organs or tissues of the body. For example, many types of common ailments, such as arthritis, bursitis, and a wide variety of other afflictions may be improved or alleviated by the localized application of ultrasonic sound waves to the affected tissue. Similarly, ultrasonic sound waves have also been used to destroy various limited groups of cells in the human body.

In some situations the same ultrasonic transducer head can be used for both diagnostic and treatment purposes. The diagnostic function of the transducer is usually accomplished at low level power inputs to the transducer head; the treatment function is usually performed at higher power levels. For example, U.S. Pat. No. 3,237,623 to Gordon discloses such a dual function for a single transducer head.

Regardless of the particular purpose for the ultrasonic waves, it is generally impractical to affix or couple the ultrasonic transducer head directly to the target body tissue to be treated or examined. Similarly, since ultrasonic energy cannot be propagated efficiently through ambient air, the transducer head cannot merely be spaced above the body. Thus, it has been customary in the prior art to utilize a waterbath as a transmitting medium for the transducer head. However, a common characteristic of all prior waterbath structures is that they are somewhat cumbersome to apply and adjust on the body and/or require partial or complete submersion of the target object in the bath.

As shown in U.S. Pat. No. 3,356,086, one common type of therapeutic waterbath structure comprises a flexible, enclosed envelope for containing the energy transmitting liquid. This envelope is designed to be wrapped around the body member to be examined (i.e. an arm). The envelope is then secured in position by various types of fastening tapes or straps. The ultrasonic transducers are attached, usually permanently, to the outside surface of the envelope. A disadvantage of such a waterbath is the difficulty in repositioning the envelope to a different body area. Whenever such a repositioning is desired, the envelope must be loosened from the area around which it was initially placed, and then moved and retied around the new area. This also necessitates a corresponding repositioning of all the electrical lead wires and other apparatus associated with the transducer head. Such an operation is both cumbersome and time-consuming.

Other types of waterbath structures have also been utilized involving relatively rigid containers for holding the energy transmitting liquid. In most cases, the transducer head is fixedly supported by and coupled to the rigid bath structure. Thus, when it is desired to reposition the bath to a different area of the body, all the equipment associated with the transducer must generally be repositioned also. As noted earlier, this is often difficult to accomplish. Consequently, a need exists for a relatively simple apparatus for using an energy transmitting liquid to couple an energy transducer to a human body, the coupling apparatus being relatively easy to reposition.

SUMMARY OF THE INVENTION

The present invention is an apparatus for operatively coupling an energy transducer to a target object (e.g. body tissue) through an energy transmitting liquid. The coupling apparatus comprises a support member suitable for positioning over or adjacent to the body tissue. A container is provided for holding the energy transmitting liquid. The container has a closed bottom portion for contacting the body tissue and a generally open top portion through which the transducer can be extended for immersion into the energy transmitting liquid held inside the container. The top portion of the container is configured so that the transducer is substantially unobstructed for movement relative to the container to allow a selective repositioning of the transducer therein. In addition, mounting means are provided for pivotably mounting the container on the support member to permit selective rotation of the container relative to the support member. Thus, the area of the body tissue being affected by the wave output from the transducer may be selectively varied over a wide range by selectively rotating the container to contact different areas of body tissue and by selectively repositioning the transducer inside the container.

BRIEF DESCRIPTION OF THE DRAWINGS

The present invention is described in conjunction with the following drawings, in which like numerals represent like elements throughout the several views.

FIG. 1 is a perspective view showing the apparatus of the present invention in which the output of an ultrasonic transducer is coupled to a human body;

FIG. 2 is a top plan view of a portion of the apparatus of FIG. 1 showing the container support frame in two relative positions; and FIG. 3 is a cross-sectional view of a portion of the apparatus of FIG. 1 showing the container for holding the energy transmitting liquid, taken alon lines 3—3 of FIG. 2.

DESCRIPTION OF THE PREFERRED EMBODIMENT

The present invention is an apparatus for coupling an ultrasonic energy source (i.e. a transducer) to living body tissue through an energy transmitting liquid. The preferred use of the present invention is in conjunction with the medical treatment of human subjects or patients. Such treatment might include the use of the transducer for therapeutic purposes on diseased tissue or for general diagnostic purposes. However, the present invention is not limited for use only with human patients. In fact, the apparatus of the present invention can be used to couple an ultrasonic energy source (i.e. transducer) to any target object. This includes animate and inanimate objects. Thus, the apparatus according to the present invention has wide utility in the general area of ultrasonic sound technology.

Referring now to FIG. 1, the apparatus is illustrated and is described in conjunction with the treatment of a human patient. The patient, depicted generally as 2, is shown lying on an examining table 4. An ultrasonic sound transducer 6 is positioned over the target area of the patient 2 which is of interest. In FIG. 1, the transducer 6 is shown as being positioned over the throat of patient 2. However, the transducer 6 could be positioned over any other desired target area or organ of the patient 2, such as the heart.

The coupling apparatus according to the present invention is generally indicated as 10 in FIG. 1. Apparatus 10 includes an elongated container 20 for holding a supply of an energy transmitting liquid 8 therein. Liquid 8 preferably comprises water, but may be any other liquid which adequately transmits acoustical energy. The container 20 itself preferably comprises a flexible bag 22 having an open top end 24 and a closed bottom end 26. Bag 22 is made of any flexible material which is impervious to the transmitting liquid 8. For example, bag 22 is preferably made of a deformable polyethylene film. However, bag 22 could be made from any other suitably flexible and water impervious material such as rubber. Because of the resiliency of bag 22, the lower portion 26 of bag 22 conforms to the shape of that area of the patient 2 which is being contacted by container 20. This allows bag 22 to contact different areas of the body of patient 2 and to conform to the shape of each area.

In addition to bag 22, container 20 also includes a relatively rigid and rectangular bag support frame 28. The upper end 24 of flexible bag 22 is fixedly attached, as by gluing, to the bag support frame 28. As seen in FIGS. 1 and 2, bag support frame 28 has four sides 30a-d which are disposed in an opposed spaced relationship relativve to one another to define an open central area 32. Two of the opposed sides 30c and 30d are also angularly curved along the arc of a circle for a purpose to be described hereafter. The open top end 24 of bag 22 is attached to the bag support frame 28 such that the open end 24 communicates with the open central area 32 of frame 28. Together the top end 24 of bag 22 and the bag support frame 28 form or define the top portion of container 20. Thus, the top portion of container 20 is, in effect, completely open.

As shown in FIGS. 1 and 3, transducer 6 is received within container 20 with the lower end 7 of the transducer immersed in the liquid 8. By virtue of the open top portion of the container 20, the transducer 6 may be inserted into the container 20 without being obstructed or supported by any portion of the container. Thus, transducer 6 can be easily moved relative to the container 20 to effect a repositioning of the transducer 6 therein. This relative movement of transducer 6 allows one to change or vary the target area of transducer 6 without repositioning the container 20. Transducer 6 is movable by suitable apparatus provided in the diagnostic machine (not shown) of which the transducer is a part. Usually this movement is accomplished by mounting transducer 6 in the end of a movable boom (not shown) or the like.

A support member 40 is provided for supporting container 20 in a suitable orientation over patient 2. Support member 40 comprises an L-shaped support bracket 42. Bracket 42 has a first vertically extending arm 44 integrally connected to a second horizontally extending arm 46. In addition, support member 40 comprises a tripod stand 48 having three legs 50 suited for engaging the ground. Tripod stand 48 further has a hollow upwardly extending socket 52 shaped for matingly receiving and supporting the vertical arm 44 of support bracket 42. A set screw 54 or similar locking device extends through socket 48 and bears against arm 44 to hold the support bracket 42 in various adjusted vertical positions.

Horizontal support arm 46 carries a substantially horizontal circular ring 60 at the end of the arm 46 which is opposite to arm 44. Ring 60 rotatably mounts container 20. In addition, ring 60 is positioned by support bracket 42 such that container 20 is located over the general area of patient 2 which is to be affected by transducer 6. A preferred vertical position for container 20 is that in which the lower portion 26 of bag 22 rests firmly but comfortably on the desired target area on the body of patient 2. Such a position can be achieved by using set screw 54 to vertically adjust the height of support bracket 42 as necessary.

Ring 60 has an inner diameter 62 of a preselected distance. In addition, ring 60 has a lip 64 integrally formed with the inner diameter 62 of the ring and extending inwardly therefrom. Lip 64 defines an annular upwardly facing support surface 66. The distance between the opposed sides 30c and 30d of the bag support frame 28 is so chosen such that the sides 30c and 30d matingly rest upon the support surface 66 defined by the lip 64. Thus, container 20 is mounted for rotation relative to the support member 40 by virtue of the resting engagement of the bag support frame 28 on the lip 64 of ring 60. Referring to FIG. 2, it is also seen that the angular curve of the sides 30c and 30d conforms to the inner diameter 62 of the ring 60. This allows smooth rotation of the container 20 relative to ring 60.

Referring to FIGS. 1 and 2, container 20 has a substantially rectangular cross-section (in a horizontal plane) which conforms to the rectangular shape of the bag support frame 28 to which the flexible bag 22 is attached at its upper end 24. Such a configuration allows a selective rotation of container 20 relative to ring 60 to vary the target area on patient 2 which is contacted by the bottom portion of container 20 and thus affected by the ultrasonic wave output from the transducer 6. Although a rectangular cross-section for container 20 has been illustrated herein, it is important only that container 20 have a non-circular configuration. For example, an elliptical configuration for container 20 would work as well as a rectangular configuration in varying the target area upon rotation of the container. Similarly, only that portion of the container which actually contacts the target area (i.e. the bottom portion) need be non-circular. Thus, container 20 could comprise a circular top portion rotatably received inside the ring 60 as long as the bottom portion of container 20 is non-circular.

Furthermore, referring to FIG. 2, container 20 having a rectangular shape fits inside the circular ring 60 with a clearance space 68 provided on either side of the container. This allows container 20 to be manually and selectively rotated by an operator. All that is required is that the operator insert his hand into one of the clearance spaces 68 and push the container 20 to a different rotative position relative to the ring 60. It is preferred that container 20 be manually adjusted to decrease the cost and complexity of coupling apparatus 2. However, suitable motor means could be provided for rotating container 20. Such a motor means would preferably include a rack and pinion engagement between the bag support frame 28 and the inner diameter 62 of ring 60 for effecting relative movement therebetween.

The transducer 6 is usually mounted on the end of a movable boom (not shown) so that the transducer may be adjustably mounted inside container 20. Not only is the transducer 6 movable along both the length and width of container 20, it is also vertically adjustable so that its lower end 7 may be positioned at different levels in the liquid 8. As shown in FIG. 3, it is desirable that the lower end 7 of transducer 6 be spaced above the target area on patient 2. There are two reasons for such a positioning. First, the ultrasonic beam emanating from transducer 6 is relatively wide adjacent the lower end 7 and becomes narrower as it proceeds outwardly therefrom. Thus, when it is desired to scan a target area on patient 2 which lies closely beneath the surface of the skin, the lower end 7 of the transducer is preferably spaced above the skin surface to locate the narrow portion of the ultrasonic beam in the target area, thereby enhancing the resolution of the ultrasonic beam. Secondly, the lower end 7 of the transducer 6 creates a considerable amount of ultrasonic "noise" which interferes with the reflections of the ultrasonic beam if the end 7 is too close to patient 2. In fact, when the target area is close to the skin surface, the use of a transducer in direct contact with the skin of patient 2 may give rise to these two undesirable effects.

It is customary in certain diagnostic machines to manually move (e.g. by hand) the transducer 6 relative to container 20 to perform scanning or diagnostic operations. It is also customary in these machines to manually hold the transducer 6 at a fixed depth in container 20. In order to simplify and ease the task of vertically holding transducer 6 in position, a transducer locating means 70 is preferably used to maintain a constant distance between the lower end 7 of transducer 6 and patient 2. Locating means 70 comprises a substantially rectangular and planar plate member 72 having a rectangular opening 74 therein. The two opposed sides 30a and 30b of support frame 28 are provided with upwardly facing support lips 76 for receiving plate member 72 in a resting engagement similar to that exhibited by frame 28 in ring 60. Plate member 72 is longitudinally slidable along the length of container 20 and the opening 74 is transversely elongated along the width of container 20. Transducer 6 extends into container 20 through the rectangular opening 74 in plate member 72. Plate member 72 is preferably made of Plexiglas or some other transparent material.

Since the transducer 6 now extends through plate member 72, an operator is able to vertically locate the transducer 6 merely by manually holding the transducer 6 vertically steady relative to plate member 72. In this regard, transducer 6 can be provided with horizontal indicia 78 or other marking lines which are aligned with plate member 72 to keep the lower end 7 of transducer 6 at the same vertical depth in container 20. In using the locating means, the operator's hand preferably encircles the transducer 6 and rests on the plate member 72 for ease of operation. Since plate member 72 is slidably mounted relative to support frame 28, the operator can longitudinally position the transducer 6 relative to the sides 30a and 30b by manually sliding plate member 72 to various adjusted positions along the support lips 76. In addition, since the transducer 6 is mounted in transversely elongated opening 74, the operator is able to transversely position transducer 6 in any longitudinal position of plate member 72 by simply moving the transducer 6 within the opening 74.

The coupling apparatus 2 according to the present invention has many advantages. First, since transducer 6 is substantially unobstructed for movement relative to container 20, the transducer may be repositioned therein by a simple transverse sliding movement of the transducer. Thus, the target area of the transducer 6 on patient 2 can be adjusted over the entire length of container 20 without having to readjust the container 20. This is substantially easier than trying to readjust a conventional transducer waterbath having the transducer fixed relative to the waterbath.

In addition, since the bottom portion of container 20 is non-circular and the container 20 is itself rotatably mounted over the patient 2, the area of contact of container 20 with the patient can be varied by selectively rotating the container 20 to various different rotative positions. Thus, an extremely large area of the patient 2 can be covered by rotating the container 20 to different positions relative to ring 60 and by repositioning the transducer 6 therein. For example, in FIGS. 2 and 3, the solid line representation depicts a first position for both the container 20 and transducer 6 relative to patient 2. However, to reach a second and different position relative to patient 2, depicted in phantom lines, it is only necessary to rotate the bag support frame 28 to reposition the container 20. Transducer 6 will also have to be repositioned to its phantom line position to keep it within container 20 and over the desired target area on patient 2. In fact, within the confines of the area bounded by the ring 60, container 20 can be rotated through a large number of different positions.

Thus, coupling apparatus 10 according to the present invention increases the possible target areas which can be covered by transducer 6 to those in the area on patient 2 bounded by ring 60. Further, coupling apparatus 10 minimizes the amount of time and effort needed to effect a repositioning of the transducer 6. Since the transducer 6 and container 20 are entirely separate and unconnected, container 20 may be repositioned without having to readjust the electrical lead wires to transducer 6 or the other apparatus associated therewith. All that is required is that transducer 6 be movably mounted on a boom or the like so that it can be kept within the container 20.

Although it is preferred that container 20 comprise a flexible bag 22 attached to a rigid bag support frame 28, various other forms for the container 20 may be utilized. However, any container 20 that is utilized should have a shoulder portion corresponding to support frame 28. This shoulder portion would be located at the upper end of the container 20 for slidably resting on the support surfacce 66 of lip 64.

In addition, it is not necessary that the top portion of the container 20 be completely open although this is preferred. For example, various types of flexible closure flaps could be used in the upper portion of the container 20 to contact and surround the transducer 6. However, such closure flaps should not afford any substantial obstruction to movement of the transducer 6 relative to the container 20. In other words, the closure flaps should only be for the purpose of sealing the top portion of the container 20, and not for the purpose of supporting transducer 6.

The transducer 6 may comprise any ultrasonic transducer suitable for use on the target subject and may be used with a variety of ancillary equipment. For example, one common use of the present apparatus is for B Mode Echocardiography in which a two dimensional cross-section of the heart is obtained. In such a case, the transducer 6 may be part of a complex diagnostic machine such as a Toshiba Sonolayergraph, Model SSL-51H. Such a machine comprises a high speed mechanical scanning drive which rotates the transducer through a predetermined sector angle. This sector angle is sufficiently large to entirely cover the particular organ being examined or treated. In addition, the transducer is mounted in a movable head so that the transducer can be positioned over different areas of the body. Such a diagnostic machine also includes a display system, such as a cathode ray tube, for displaying the information received from studying the reflections of the transducer 6 off of the organ under study.

Various other modifications would be apparent to those skilled in the art. Therefore, the scope of the invention is to be limited only by the following claims.

I claim:

1. Apparatus for operatively coupling an ultrasonic energy source to a target object, which comprises:
   (a) a support member suitable for positioning adjacent to the target object;
   (b) a container for holding an energy transmitting liquid, the container including a closed bottom portion having a noncircular cross-sectional configuration for contacting the target object, and a top portion through which the ultrasonic energy source extends for immersion in the energy transmitting liquid held in the container, the top portion being so configured such that the ultrasonic energy source is substantially unobstructed for movement relative to the container to allow a selective repositioning of the ultrasonic energy source therein; wherein the top portion of the container is completely open allowing the ultrasonic energy source to be inserted into the energy transmitting liquid without touching any portion of the container, and in which the container comprises:
      (i) a polygonal shaped support frame having a plurality of sides which surround and define an open central area;
      (ii) a flexible bag having a first open end and a second closed end; and
      (iii) means for attaching the flexible bag in an opened orientation to the support frame such that the open end of the bag communicates with the open central area of the support frame to define the open top portion of the container; and
   (c) support means for pivotably mounting the container on the support member for selective rotation relative thereto about a substantially vertical axis such that the bottom portion of the container is able to contact different areas of the target object, whereby the area of the target object being affected by the output of the ultrasonic energy source may be selectively varied by selectively rotating the container and by selectively repositioning the ultrasonic energy source inside the container, in which the support means for mounting the container comprises:
      (i) a substantially circular ring attached to the support member, the ring having an inner diameter and a substantially horizontal support surface positioned adjacent to and inwardly of the inner diameter; and
      (ii) at least two of the sides of the support frame being spaced apart in an opposed relationship, the two opposed sides being spaced apart a sufficient distance such that the container is rotatably supported on the ring by a resting engagement of the two opposed sides of the support frame on the horizontal support surface of the ring.

2. A coupling apparatus as recited in claim 1, in which the horizontal support surface is defined by a lip protruding inwardly from the inner diameter of the ring.

3. Apparatus for operatively coupling an ultrasonic energy source to a target object, which comprises:
   (a) a support member suitable for positioning adjacent to the target object;
   (b) a container for holding an energy transmitting liquid, the container including a closed bottom portion having a noncircular cross-sectional configuration for contacting the target object, and a top portion through which the ultrasonic energy source extends for immersion n the energy transmitting liquid held in the container, the top portion being so configured such that the ultrasonic energy source is substantially unobstructed for movement relative to the container to allow a selective repositioning of the ultrasonic energy source therein; and
   (c) means for pivotably mounting the container on the support member for selective rotation relative thereto such that the bottom portion of the container is able to contact different areas of the target object, wherein the mounting means for the container comprises:
      (i) a substantially circular ring attached to the support member in a substantially horizontal orientation, the ring having an inner diameter and a lip protruding inwardly from the inner diameter, the lip defining an upwardly facing horizontal support surface; and (ii) the top portion of the container being provided with an outwardly protruding shoulder which matingly engages the horizontal support surface defined by the lip such that the container is rotatably supported by the ring, whereby the area of the target object being affected by the output of the ultrasonic energy source may be selectively varied by selectively rotating the container and by selectively repositioning the ultrasonic energy source inside the container.

4. Apparatus for operatively coupling an ultrasonic energy source to a target object, which comprises:

(a) a support member suitable for positioning adjacent to the target object;

(b) a container for holding an energy transmitting liquid, the container including a closed bottom portion having a noncircular cross-sectional configuration for contacting the target object, and a top portion through which the ultrasonic energy source extends for immersion in the energy transmitting liquid held in the container, the top portion being so configured such that the ultrasonic energy source is substantially unobstructed for movement relative to the container to allow a selective repositioning of the ultrasonic energy source therein;

(c) means for pivotably mounting the container on the support member for selective rotation relative thereto such that the bottom portion of the container is able to contact different areas of the target object, whereby the area of the target object being affected by the output of the ultrasonic energy source may be selectively varied by selectively rotating the container and by selectively repositioning the ultrasonic energy source inside the container; and (d) wherein the container is provided with means for vertically locating the ultrasonic energy source relative to the bottom portion of the container, in which the locating means comprises a substantially horizontal plate member slidably mounted at a predetermined vertical location on the container for movement in a first direction relative to the container, the plate member having an elongated opening therein which relative to the container extends in a second direction substantially perpendicular to the first direction, the opening being configured to loosely receive the ultrasonic energy source for vertical alignment of the ultrasonic energy source with the plate member.

5. Apparatus for operatively coupling an ultrasonic energy source to a target object, which comprises:

(a) a support member suitable for positioning adjacent to the target object, the support member including a substantially circular, horizontal and upwardly facing support surface;

(b) a container for holding an energy transmitting liquid, the container including a bottom portion for contacting the target object and a top portion through which the ultrasonic energy source extends for immersion in the energy transmitting liquid held in the container, and the container having outwardly protruding shoulder means located above the bottom portion thereof for matingly engaging and resting upon the horizontal support surface, whereby the container is pivotably supported by the support surface for rotation about a substantially vertical pivot axis through the container; and (c) wherein the bottom of the container has a cross-sectional configuration whose shape is selected in conjunction with the location of the pivot axis such that rotation of the container varies the area of the target object being contacted by the bottom portion of the container.

6. A coupling apparatus as recited in claim 5, further including a ring attached to the support member, the ring having an opening through which the container extends; and wherein the horizontal support surface is defined by a circular lip protruding inwardly from the opening of the ring.

7. A coupling apparatus as recited in claims 5 or 6, wherein the shoulder means on the container is defined by a polygonal shaped support frame having a plurality of sides, at least two of the sides of the support frame being spaced apart in an opposed relationship by a sufficient distance to allow the container to be rotatably supported by a resting engagement of the two opposed sides on the horizontal support surface of the support member.

* * * * *

UNITED STATES PATENT AND TRADEMARK OFFICE
CERTIFICATE OF CORRECTION

PATENT NO. : 4,185,502

DATED : January 29, 1980

INVENTOR(S) : Ralph Frank

It is certified that error appears in the above-identified patent and that said Letters Patent are hereby corrected as shown below:

In column 1, line 22, for "lond" read --long--.

In column 3, line 11, for "relative" read --rotative--.

line 14, for "alon" read --along--.

In column 4, line 1, for "relativve" read --relative--.

In column 5, line 39, for "mounted" read --positioned--.

In column 8, line 53, for "n" read --in--.

Signed and Sealed this

Twenty-ninth Day of April 1980

[SEAL]

Attest:

*Attesting Officer*

SIDNEY A. DIAMOND

*Commissioner of Patents and Trademarks*